United States Patent
Hagele

(10) Patent No.: US 6,632,202 B1
(45) Date of Patent: Oct. 14, 2003

(54) PRECISION RELEASE EYE DROPPER BOTTLE

(76) Inventor: James Hagele, 13262 Evergreen Dr., Nevada City, CA (US) 95959

( * ) Notice: Subject to any disclaimer, the term of this patent is extended or adjusted under 35 U.S.C. 154(b) by 0 days.

(21) Appl. No.: 09/272,066

(22) Filed: Mar. 16, 1999

(51) Int. Cl.$^7$ .......................... A61M 35/00; B65D 47/18
(52) U.S. Cl. ........................................ 604/295; 222/420
(58) Field of Search ................ 604/294–302; 222/211, 420, 421, 422

(56) References Cited

U.S. PATENT DOCUMENTS

| | | | |
|---|---|---|---|
| 1,900,201 A | | 3/1933 | Sager |
| 2,728,491 A | * | 12/1955 | Aneshansley ............... 222/158 |
| 2,734,665 A | * | 2/1956 | Flamm ....................... 222/207 |
| 3,261,355 A | | 7/1966 | Burbig |
| 3,756,478 A | * | 9/1973 | Podell et al. ............... 222/211 |
| 5,007,905 A | | 4/1991 | Bauer |
| 5,030,214 A | | 7/1991 | Spector |
| 5,069,675 A | | 12/1991 | Menchel et al. |
| 5,127,553 A | | 7/1992 | Weinstein |
| 5,373,964 A | * | 12/1994 | Moore .......................... 222/1 |
| 5,431,314 A | * | 7/1995 | Bonnelye et al. ........... 222/420 |
| 5,588,559 A | * | 12/1996 | Vallet Mas et al. ......... 210/445 |
| 5,611,788 A | | 3/1997 | Marchment |
| 6,041,978 A | * | 3/2000 | Hagele ....................... 222/211 |

* cited by examiner

Primary Examiner—Weilun Lo
Assistant Examiner—Linh Truong

(57) ABSTRACT

An eye dropper bottle 20 is provided which allows a person to instill drops D into an eye E while the bottle 20 is held in a near horizontal orientation 22. The bottle 20 has a reservoir 51 for holding a liquid 59. The reservoir 51 includes a base 52, an upper end 50, and compressible walls 55. The bottle 20 further includes a neck 40 into which a dropper tip 34 fits. The neck 40 has external threads 42 onto which an internally threaded 32 cap 30 fits. The internal surface 56 of the walls 55 of the reservoir 51 maintains a constant slope 58 of a predetermined angle to allow virtually all the liquid 59 of the reservoir 51 to flow toward a dropper tip 34 where it can be discharged in the form of drops D while the bottle is held in a near horizontal orientation 22.

The bottle 20 is grasped with a thumb T parallel to the length of the bottle 20 and an index finger F wrapped around a sulcus 48. The bottle is held in a near horizontal orientation over an eye E with the nail N of the thumb T resting against the upper bridge B of the nose. A predetermined distance 45 between a flange 44 and the distal end 36 of the dropper tip 34 causes the drop D to consistently and accurately align with an eye E.

Drops D may also be instilled by holding the bottle 20 above and over an eye E in a near horizontal orientation 22.

5 Claims, 4 Drawing Sheets

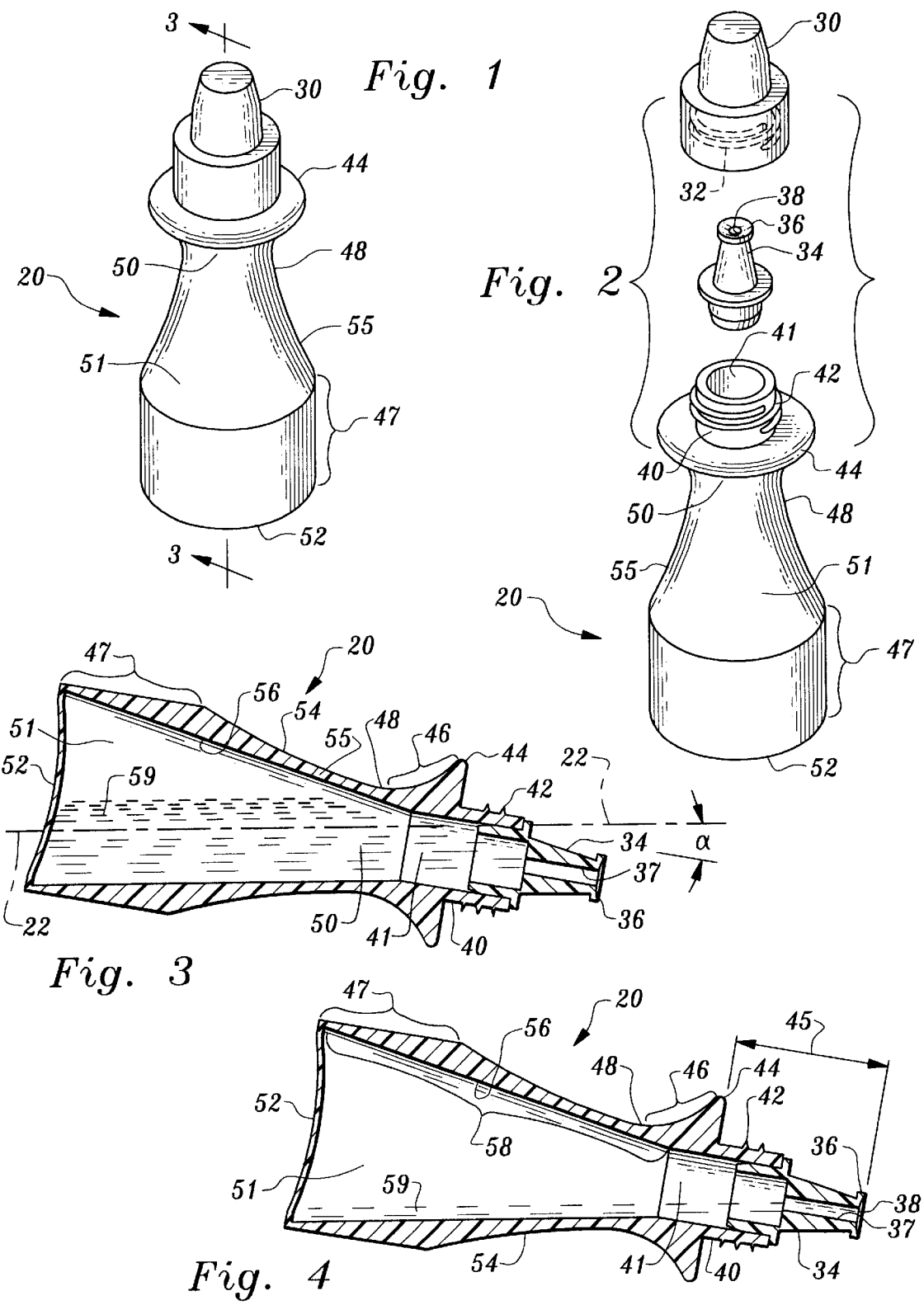

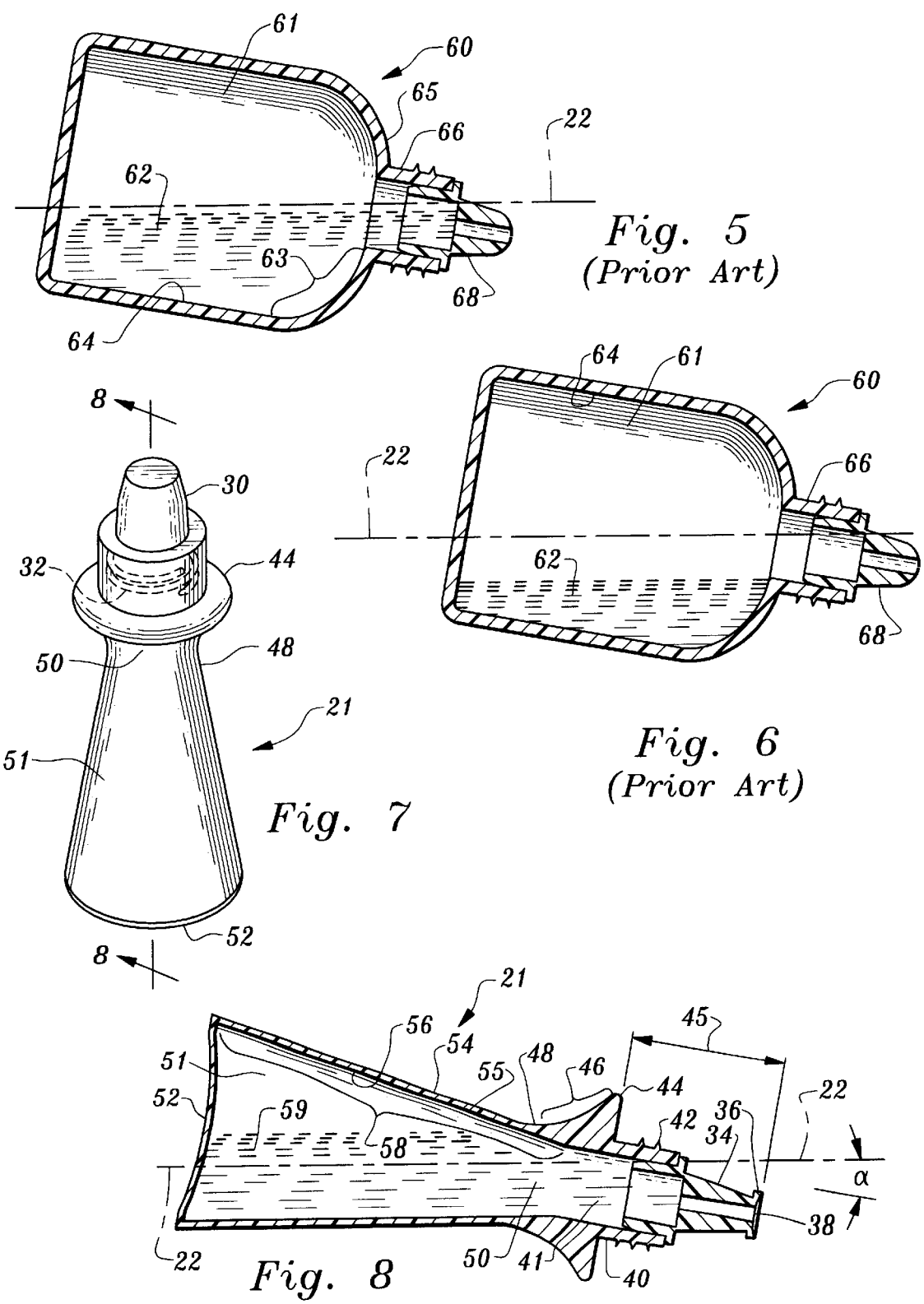

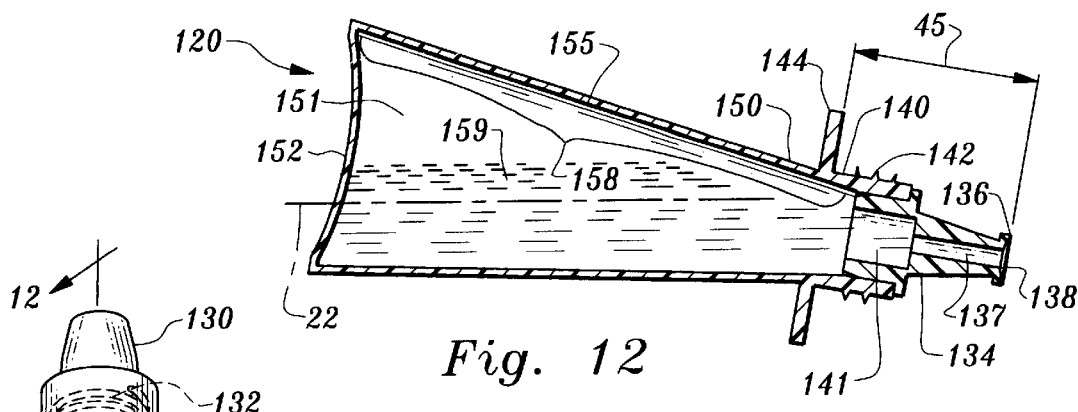
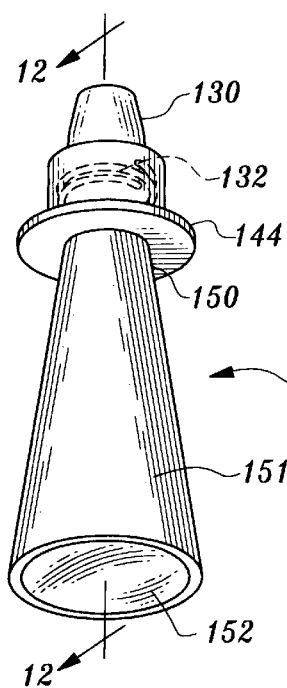
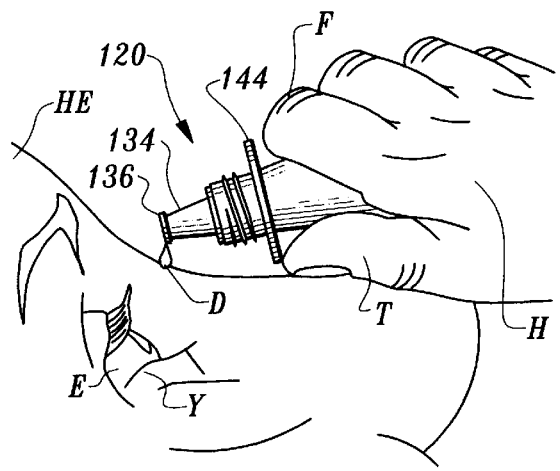
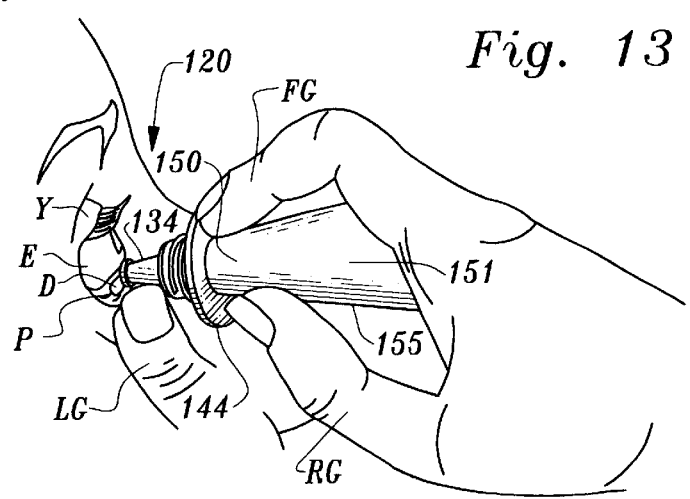
Fig. 11
Fig. 12
Fig. 13
Fig. 14

PRECISION RELEASE EYE DROPPER BOTTLE

FIELD OF INVENTION

This invention relates to eye dropper bottles for dispensing liquids. More particularly, this invention relates to bottles for instilling medicinal liquids into a person's eye while the head is tilted back and the bottle is held against the bridge of the nose in a near horizontal orientation. This invention also is used for instilling drops into an eye by tilting the head back and holding the bottle in a near horizontal orientation with the dropper tip above and over an eye.

BACKGROUND OF THE INVENTION

The instillation of medicinal eye drops tends to be difficult and annoying for many individuals. Generally, a person tilts their head back and looks up. Simultaneously, the dropper bottle is elevated above the eye and held in an inverted position while the walls are squeezed, causing the drop to fall toward the eye. If the lower eyelid is retracted down at the same time, the drop will more easily find its target.

Often, however, the drop misses the eye altogether and falls on the face, where it has no therapeutic value and may even be irritating to the skin. Or, several drops might be released if there is a momentary delay in the first drop and a second one is squeezed from the bottle, causing an overdose and waste of medicine.

There are several factors that often complicate the conventional way of instilling eye drops. First, it is difficult for some individuals, especially the elderly, to elevate their shoulder high enough to place the eye dropper in an ideal position above the eye. Secondly, limitation of motion of the hand or the wrist makes it difficult to turn the bottle in a substantially inverted position. Thirdly, some individuals, as they grow older, find that their hands and head are no longer steady, thus posing the problem of not being able to maintain proper alignment while the drops are being instilled. It is interesting that many patients, even without these limitations, confess that they are never sure where the drop will fall, even though they use drops on regular, daily basis.

It is important to note that dozens of new medications to treat various ocular conditions are discovered and produced every year. There has been tremendous advances in the treatment of ocular diseases, especially in the field of glaucoma. Hundreds of millions of bottles of eye drops are produced each year for this condition alone. Yet, in spite of all the advances in the medications themselves, little or no progress over the past 40 years or more has been made in the way the drops are delivered to the patient.

Billions of dollars are spent annually just to treat glaucoma. It would be interesting to know what percentage of those billions of dollars are wasted because of the present delivery system for these medications. Presently, insurance companies, health maintenance organizations, governmental agencies and especially patients are concerned about the cost of treating various medical conditions. It is essential that the delivery system for ocular medications be reexamined and improved.

There are some individuals who are unable to administer their own drops and either rely on a spouse or a caregiver to instill them. Often the caregiver finds it difficult to get the patient to open their eyes widely while the drops are being instilled. When the hand of the assistant comes before the eye holding the bottle vertically and obscuring the vision, there is a very strong protective reflex to close the eyelids. This makes it difficult to instill the drops with any accuracy and often the drop misses the eye and runs down the cheek. At that point one doesn't know if a drop or a portion of a drop did indeed get into the eye.

The vast majority of individuals administer their own drops and it is imperative to devise a better delivery system for the benefit of these individuals. It is important that the condition for which the drops are taken is adequately treated and that waste is kept to an absolute minimum.

Some attempts have been made over the years to improve the way drops are instilled into the eye. The prior art shows such devices as eye cups that screw onto the threads of a standard eye dropper bottle. Two such prior art eye dropper bottles are described in the patents to Spector (U.S. Pat. No. 5,030,214) and to Bauer (U.S. Pat. No. 5,007,905). However, the bulkiness of these devices, problems with maintaining sterility, and the tremendous variation in bottle sizes, all keep these devices from being widely used. Also, prior art shows attempts have been made to place various devices, such as an angled spout, on the end of an eye dropper bottle to better direct the drop into the eye. One such prior art eye dropper bottle is described in the patent to Menchel et al. (U.S. Pat. No. 5,069,675). Again, it has not solved the delivery system problems that exist.

Today's standard eye dropper bottles are designed in such a way that for all the liquid of the bottle to be used, the bottle must be virtually turned upside down. This is especially true as the volume of liquid decreases in the bottle. This is necessary because the slope of the internal surface of the reservoir of the bottle is flat except for the upper end of the bottle where the slope abruptly changes and turns toward the outlet. The angle that is formed is nearly 90 degrees. It is essential for all the liquid in the reservoir to flow toward the tip so it can be released from the bottle. However, with today's standard eye bottles, a large portion of the liquid remains in the reservoir when the bottle is held in a horizontal position.

A standard 15 ml. (milliliters) eye bottle, without a tip and held in a perfectly horizontal position, will retain 35% of the liquid in the bottle. In other words, 65% of the liquid in the bottle will run out spontaneously, but the remaining 35% of the liquid will not flow out the bottle opening because of the slope of the internal surface of the upper end of the reservoir.

One of the standard 5 ml. dropper bottles on the market today, holding approximately 140 drops, has been observed to retain 50 drops in the bottle when the upper end of the bottle is held down at a 10 degree angle. This same bottle retains 20 drops when that angle is increased to 40 degrees. In fact, the bottle must be held down almost 80 degrees to have virtually all the liquid flow out of the bottle.

Not only do the currently produced bottles need to be held in a markedly down position to empty the bottle, but the bottle needs to be held down to avoid the drop from adhering to the surface of the tip, where it refuses to fall. This adherence of the drop to the tip of the bottle is caused by molecular adhesion or surface tension. The force of molecular adhesion acting upon the drop can be greater than the force of gravity. If a drop adheres to the tip, the patient will squeeze out a second drop which will either fall or further migrate down the surface of the tip. In those circumstances often the drop will fall from the threaded portion of the neck of the bottle. When this occurs the drop usually misses the target altogether. One can readily see where considerable waste can occur.

Not only is an improved bottle needed, but an improved dropper tip to complement such a bottle is mandatory.

(A dropper tip to complement the present invention has been designed that makes drop instillation more accurate, consistent and simultaneously prevents drops from adhering to the stem of the dropper tip. A patent for such a newly designed dropper tip has been filed with the U.S. Patent and Trademark Office; Titled, "Precision Release Tip For Medicinal Liquid Dropper"; Inventor, James Hagele; PTO Application Number, 09/156,216; Filing Date, Sep. 18, 1998; Preliminary Class, 222.)

SUMMARY OF THE INVENTION

The present invention addresses the problems associated with placing drops into an eye in a consistent and precise manner with minimum waste. A bottle has been designed in which the internal surface of the walls of the reservoir maintains a constant slope between the base and the upper end of the reservoir. The constant slope of the internal surface converges from a larger diameter base toward a smaller diameter upper end of the reservoir. This results in a conically-shaped reservoir to hold the liquid. The slope has a predetermined angle of such a degree that virtually all the liquid in the reservoir of the bottle will flow toward the tip when the bottle is held in a near horizontal orientation.

In contrast, the external surface of the walls of the reservoir has a varied slope. At the upper end of the reservoir, the external surface makes a sharp curved angle away from the internal surface and fuses into a flange. This curved slope at the upper end of the bottle forms a broad sulcus or depression, shaped in such a way that the thumb and fingers fit perfectly into it. The thumb is held parallel to the length of the bottle and the index finger wraps around the opposite side of the suldus. Thus, the bottle can always be grasped and held in the exact same manner. This grip on the bottle also provides a secure way of holding the bottle.

At the upper end of the sulcus is an encircling flange which acts as a stop for the thumb and fingers to grip against. It is important that the bottle be held exactly the same each time in order to produce a consistent and precise method of instilling drops into an eye. The flange and sulcus of the bottle help to create this consistency.

The preferred method for instilling drops into the eye is described. The eye dropper bottle is grasped and held in the manner described above. The head of the user is tilted back and the eye is opened widely. The bottle is then turned horizontally and placed across the bridge of the nose with the thumbnail resting flatly on the upper part of the bridge of the nose. When the nail of the thumb is placed against the bridge of the nose in this manner, the base of the bottle automatically becomes slightly elevated, causing the liquid in the reservoir of the bottle to flow toward the tip of the dropper where it can be discharged. This method results in an accurate and consistent positioning of the bottle over the eye.

The distance from the flange to the distal end of the dropper tip has been predetermined so that there is a precise alignment with the dropper tip and the eye. When the proper positioning has been achieved, the user compresses the walls of the bottle with the fingers, causing a drop to fall into the eye. Keeping the thumbnail flat against the bridge of the nose also protects from touching either the eye or the eyelid with the tip of the bottle. This process is simply reversed when the other eye is treated; the right hand holding the bottle for the left eye and the left hand holding the bottle for the right eye. All these factors result in an easier, more accurate, and consistent way of instilling eye drops. When patients are having difficulty placing drops into their eyes in the conventional way and are shown this method, they usually comment how much easier it is for them.

There are some situations where an individual is unable to tilt their head back far enough to cause the drop to fall into the eye. In those cases, the thumb holding the bottle against the bridge of the nose can be rotated slightly upward, causing the tip of the bottle to be higher above the eye. Also, the individual with limitation of motion of the neck may retract the lower eyelid with the fingers of the other hand and thereby provide a wider opening of the target area for drop instillation.

An alternate method of instilling drops into the eye with the present invention is also presented. For those individuals who wish to use the more conventional method of instilling drops into the eye, yet desire the added benefits of the present invention, the following method is given. The bottle is grasped and held by the thumb and fingers exactly as described in the preferred method above. However, instead of placing the bottle across the bridge of the nose, the bottle is held in a near horizontal orientation above and over a widely opened eye. Alignment is made by sighting the end of the tip of the bottle directly over the eye. Compressing the walls of the bottle causes the release of a drop into the eye. This method requires only slight elevation of the shoulder and virtually no rotation of the hand or wrist and both eyes can be treated without changing hands. Aligning the tip of the dropper with the eye is easier when the bottle is held in a near horizontal position than when pointing the bottle down at the eye.

For those individuals who are unable to administer their own drops and must rely on someone else, the present invention is of great help. The outer lower eyelid of the eye is retracted down and out by the caregiver, creating a small pocket in the lower eyelid. The bottle of the present invention is brought up from the side of the face and held in a near horizontal orientation while the drop is made to fall into this created pocket. This method is much less threatening to the patient than holding the bottle vertically in front of the eye. Usually, if done quickly and properly, the patient will hardly know the drop was instilled.

Thus, the present invention of a "Precision Release Eye Dropper Bottle" provides a more accurate way of instilling drops and simultaneously gives the patient an easier and more consistent delivery system for eye medications. It also has the great benefit of minimizing the waste of eye drops.

OBJECTS OF THE INVENTION

A primary object of the present invention is to provide an eye liquid dispensing bottle that allows virtually all the liquid in the bottle to be discharged therefrom in the form of drops while held in a near horizontal orientation.

Another object of the present invention is to provide an eye dropper bottle configured to be grasped and held exactly in the same manner each time it is used.

Another object of the present invention is to provide a bottle configured to give an accurate and consistent alignment between the tip of the dropper and an eye for precise drop instillation.

Another object of the present invention is to provide an eye dropper bottle which maximizes utilization of the medicinal liquid within the reservoir, thereby avoiding waste.

Another object of the present invention is to provide a bottle which minimizes the number of drops which might fall on the skin of the face rather than in an eye.

Another object of the present invention is to provide an eye bottle configured to be supported against the bridge of the nose for both alignment and ease of eye drop instillation.

Another object of the present invention is to provide a bottle configured to be held in a near horizontal orientation by an individual with restricted hand, wrist, or shoulder movements.

Another object of the present invention is to provide a bottle configured to be supported against the bridge of the nose for those individuals with an unsteady hand or head.

Another object of the present invention is to provide a bottle whereby a caregiver, by holding the bottle in a near horizontal orientation below the line of vision and to the side, can more easily instill drops inside the eyelid of an individual unable to do so for himself/herself.

Another object of the present invention is to provide an eye dropper bottle configured to either be used by holding the bottle above and over an eye or by holding the bottle against the bridge of the nose for drop instillation.

Other further objects of the present invention will become apparent from a careful reading of a background of the invention, a summary of the invention, a detailed description of the invention, the drawings, and the claims.

BRIEF DESCRIPTION OF THE DRAWINGS

FIG. 1 is a perspective view of an assembled most preferred embodiment of the present invention.

FIG. 2 is an exploded perspective view of the most preferred embodiment of the present invention.

FIG. 3 is a sectional view 3—3 of FIG. 1 of the most preferred embodiment of the present invention with a large amount of liquid present in the reservoir.

FIG. 4 is a sectional view 3—3 of FIG. 1 of the most preferred embodiment of the present invention with minimal liquid present in the reservoir.

FIG. 5 is a sectional view of a prior art bottle in a near horizontal orientation with a large amount of fluid present in the reservoir.

FIG. 6 is a sectional view of a prior art bottle in a near horizontal orientation with a smaller amount of fluid present in the reservoir.

FIG. 7 is a perspective view of an assembled preferred embodiment of the present invention.

FIG. 8 is a sectional view 8—8 of FIG. 7 of a preferred embodiment of the present invention with a reservoir filled with liquid.

FIG. 11 is a perspective view from below of an assembled alternative embodiment of the present invention.

FIG. 12 is a sectional view 12—12 of FIG. 11 of an alternative embodiment of the present invention with a large amount of liquid present in the reservoir.

FIG. 13 is a side elevation of an alternative embodiment of the present invention demonstrating drop instillation into an eye while holding the present invention above and over an eye with the head tilted back.

FIG. 14 is a side elevation of an alternative embodiment of the present invention demonstrating drop instillation by a caregiver into a created pocket of the lower eyelid, while the present invention is held from the side and below the line of vision in a near horizontal orientation.

DESCRIPTION OF THE PREFERRED EMBODIMENT

Figure 9:
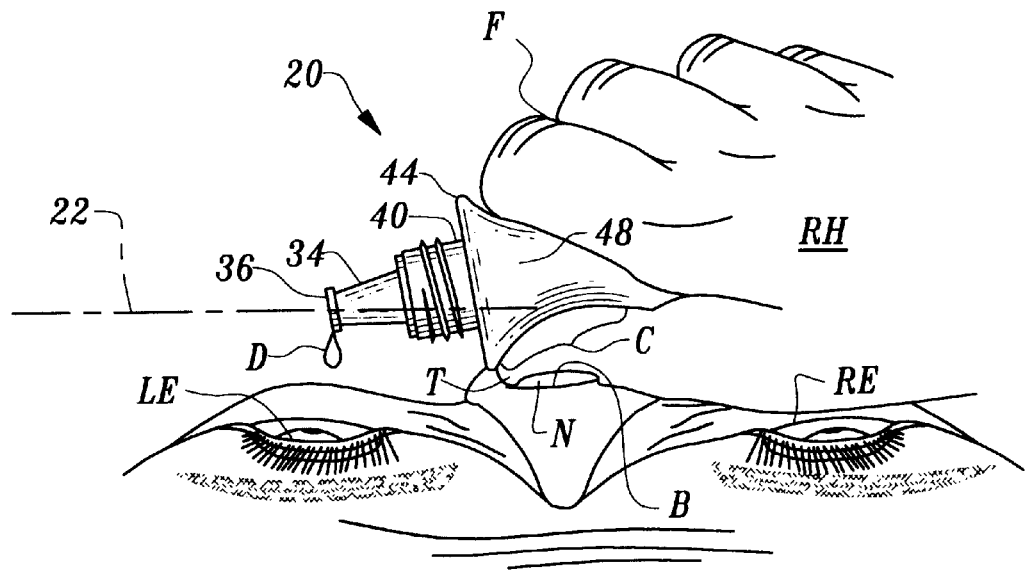
FIG. 9 is a view of the most preferred embodiment of the present invention from behind and above a head that is tilted back. Demonstrated is a drop being instilled into a left eye with a right thumbnail positioned against the upper bridge of a nose and the present invention being held by a right hand.

Referring to the drawings wherein like reference numerals represent like parts throughout the various drawing figures, reference numeral 20 (FIGS. 2, 3, 9) is directed to a bottle for instilling drops D of liquid 59 into a person's eye E. The most preferred embodiment eye bottle 20 consists of a reservoir 51 with a larger diameter base 52 and a smaller diameter upper end 50. The reservoir walls 55 connect the base 52 with the upper end 50.

The bottle 20 further includes a sulcus 48 for grasping and holding the bottle 20. A flange 44 is sandwiched between the upper end 50 and a neck 40 of the bottle 20. The neck 40 has external threads 42 which fit an internally threaded 32 cap 30. This union forms a male-female type locking assembly. The cap 30 tightens against the flange 44. The neck 40 has an opening in its center 41 into which a dropper tip 34 fits. The cap 30 is screwed onto the external threads 42 of the neck 40 to prevent loss of liquid 59 from the reservoir 51 and prevent contamination of both the dropper tip 34 and the liquid 59 of the reservoir 51.

More specifically, and with particular initial reference to FIGS. 3, 4, the details of the most preferred embodiment of the bottle 20 of the present invention are described. The walls 55 of the reservoir 51 consist of an internal surface 56 and an external surface 54. The internal surface 56 of the reservoir walls 55 maintains a constant slope 58 between the base 52 and the upper end 50 of the reservoir 51. The constant slope 58 of the internal surface 56 converges from a larger diameter base 52 to a smaller diameter upper end 50, forming a conically-shaped reservoir 51. This constant slope 58 is of a predetermined angle to allow virtually all the liquid 59 of the reservoir 51 to flow toward the dropper tip 34 when the bottle 20 is held in a near horizontal orientation 22. A small angle α is formed between a horizontal line 22 and the angle of the bottle 20.

The external surface 54 of the reservoir walls 55 has a varied slope between the base 52 and the upper end 50. The external surface 54 of the reservoir walls 55 is of such a slope that the diameter of the bottle 20 remains the same externally at its lower portion 47. The external surface 54 of the upper end 50 of the reservoir 51 curves sharply outward and away from the internal surface 56. The sharp curve 46 of the upper end 50 of the reservoir 51 forms a sulcus 48. The thumb T and the index finger F (FIGS. 9, 10) fit perfectly into the sulcus 48 which provides for grasping and holding the eye bottle 20.

A flange 44 (FIGS. 3, 4) is formed at the end of the sharp curve 46 of the external surface 54 of the upper end 50 of the reservoir 51. The flange 44 encircles the upper end 50 of the reservoir 51 and is sandwiched between the upper end 50 of the reservoir 51 and the neck 40 of the bottle 20. The flange 44 provides a stop for the thumb T and index finger F to grip against. The predetermined distance 45 between the flange 44 and the distal end 36 of the dropper tip 34 provides for consistent and accurate instillation of an eye drop D into an eye E.

FIG. 3 depicts a reservoir 51 with a large volume of liquid 59 present. This liquid 59 is able to flow freely toward the tip of the dropper 34 when the bottle 20 is held in a near horizontal orientation 22. In FIG. 4 the volume of liquid 59 of the reservoir 51 is greatly diminished, yet the slope 58 of the internal surface 56 of the reservoir 51 allows virtually all the liquid 59 to flow toward the tip 34 where it can be discharged in the form of drops D.

In FIGS. 5, 6, a prior art bottle 60 is depicted with liquid 62 present in a reservoir 61. The internal surface of the reservoir wall 64 forms a nearly perpendicular angle 63 at the upper end 65 of the reservoir 61. In the drawings of the prior art, bottle 60 has a neck 66 into which a dropper tip 68 is housed. One can readily see the internal surface slope 63 prevents approximately one-third of the liquid 62 in the reservoir 61 to reach the dropper tip 68 when the bottle 60 is held in a near horizontal orientation 22. In fact, the bottle 60 must be nearly inverted in order for all the liquid 62 in the reservoir 61 to be discharged.

FIGS. 7, 8 are a preferred embodiment of an eye bottle 21 for instilling drops D of liquid 59 into a person's eye E. The bottle 21 further includes a sulcus 48 for grasping and holding the bottle 21. A flange 44 is located between the upper end 50 and the neck 40 of the bottle 21. The neck 40 has external threads 42 which fit an internally threaded 32 cap 30. The cap tightens against the flange 44. The neck 40 has an opening in its center 41 into which a dropper tip 34 fits.

More specifically, and with particular initial reference to FIG. 8 the details of the preferred embodiment of the bottle 21 of the present invention are described. The walls 55 of the reservoir 51 consist of an internal surface 56 and an external surface 54. The internal surface 56 of the reservoir walls 55 maintains a constant slope 58 between the base 52 and the upper end of the reservoir 50. This constant slope 58 is of a predetermined angle to allow virtually all the liquid 59 of the reservoir 51 to flow toward the dropper tip 34 when the bottle 21 is held in a near horizontal orientation 22.

The external surface 54 of the reservoir walls 55 has a varied slope between the reservoir base 52 and the reservoir upper end 50. The external surface 54 of the reservoir 51 curves sharply outward and away from the internal surface 56 at the upper end 50 of the reservoir 51. The sharply outward curve 46 of the upper end 50 of the reservoir 51 forms a sulcus 48. The thumb T and the index finger F fit perfectly into the sulcus 48 which provides for grasping and holding the eye dropper bottle 21.

A flange 44 is formed at the end of the sharp curve 46 of the external surface 54 of the walls 55 of the upper end 50 of the reservoir 51. The flange 44 encircles the upper end 50 of the reservoir 51 and is sandwiched between the upper end 50 and the neck 40 of the bottle 21. The flange 44 provides for a stop for the thumb T and the index finger F to grip against. A predetermined distance 45 between the flange 44 and the distal end 36 of the dropper tip 34 provides for consistent and accurate instillation of an eye drop D into an eye E.

Figure 10:
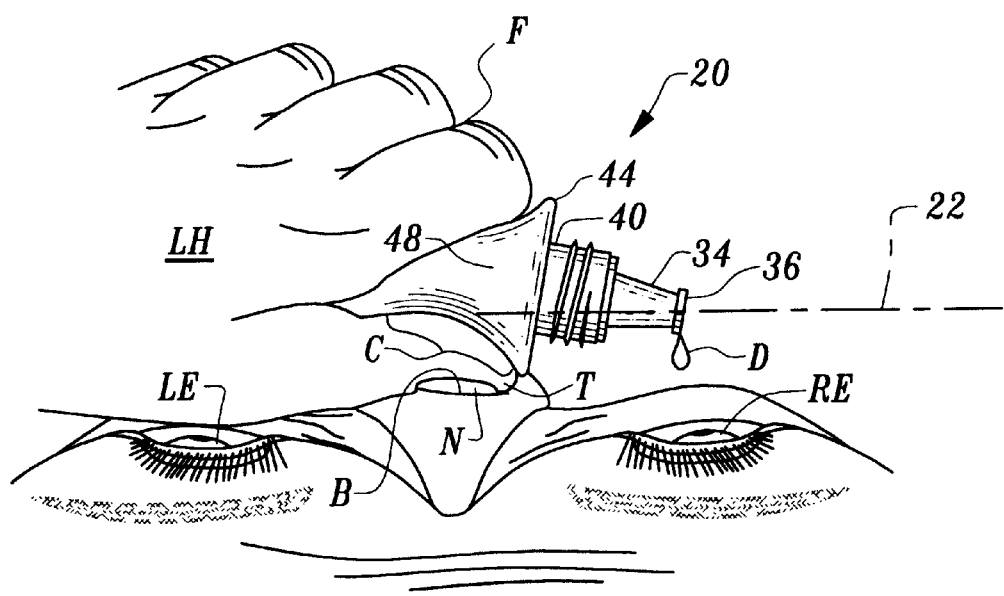
FIG. 10 is a view of the most preferred embodiment of the present invention from behind and above a head that is tilted back. Demonstrated is a drop being instilled into a right eye with the left thumbnail positioned against the upper bridge of a nose and the present invention held by a left hand.

A method for instilling an eye drop D into an eye E using the most preferred embodiment bottle 20 is shown in FIGS. 9, 10. In FIG. 9 the right hand RH is shown holding the bottle 20 with a thumb T held parallel to the length of the bottle 20 and an index finger F wrapped around the sulcus 48. The flange 44 provides for a stop for the thumb T and index finger F to grip against. The bottle 20 is placed in a near horizontal orientation 22 above and over an opened left eye LE by resting the thumbnail N against the upper bridge of the nose B. By placing the thumbnail N flat against the bridge of the nose B, the curvature of the thumb C causes the reservoir base 52 to become slightly elevated, allowing virtually all the reservoir liquid 59 to flow toward the dropper tip 34. The predetermined distance 45 between the flange 44 and the distal end of the tip 36 (FIG. 8) provides for consistent and accurate positioning. The thumb T and index finger F apply pressure to the compressible walls 55 of the bottle 20 and cause a drop D to fall into an eye E.

FIG. 10 is a method as described above in FIG. 9 except a left hand LH is used to instill a drop D into a right eye RE.

A preferred embodiment eye bottle 120 for instilling drops D of liquid 159 into a person's eye E is shown in FIGS. 11, 12. The bottle 120 consists of a reservoir 151 with a larger diameter base 152 and a smaller diameter upper end 150. The bottle further includes a flange 144 sandwiched between an upper end of the reservoir 150 and a neck 140. The neck 140 has external threads 142 which fit an internally threaded 132 cap 130. The cap 130 tightens against the flange 144. The neck 140 has an opening in its center 141 into which a dropper tip 134 fits. The cap 130 is screwed onto the threads of the neck 140 to prevent loss of liquid from the reservoir 151 and also prevent contamination of both the dropper tip 134 and the liquid 159 of the reservoir 151. More specifically, and with particular initial reference to FIG. 12, the details of the preferred embodiment of the bottle 120 of the present invention are described. The walls 155 of the reservoir 155 maintain a constant slope 158 between the base 152 and the upper end of the reservoir 150. This constant slope 158 of the walls 155 of the reservoir 151 is of a predetermined angle to allow virtually all of the liquid 159 of the reservoir 151 to flow toward the dropper tip 134 when the bottle 120 is held in a near horizontal orientation 22.

The upper end of the reservoir 150 provides an area for grasping and holding the bottle 120 with a thumb T and index finger F of a hand H. A flange 144 is formed at the upper end of the reservoir 150. The flange 144 encircles the upper end 150 of the reservoir 151 and is sandwiched between the upper end 150 and the neck 140 of the bottle 120. The flange 144 provides for a stop for the thumb T and the index finger F to grip against. A predetermined distance 45 between the flange 144 and the distal end 136 of the dropper tip 134 provides for consistent and accurate instillation of an eye drop D into an eye E.

A method for instilling an eye drop D into an eye E using the preferred embodiment bottle 120 is demonstrated in FIG. 13. A hand H grasps the bottle 120 by placing a thumb T parallel to the length of the bottle 120 and the index finger F is wrapped around the upper end 150 of the reservoir 151 and grips against the flange 144. The head HE of the patient is tilted back, the eye E is opened widely and the bottle 120 is held in a near horizontal orientation 22 above and over the eye E. Applying digital pressure to the walls of the reservoir 155 causes the release of a drop D into an eye E.

The preferred embodiment bottle 120 may also be used as demonstrated in FIGS. 9, 10.

A method is shown in FIG. 14 whereby a caregiver places a drop D into an eye E of a patient in the following manner. A left thumb LG of the caregiver retracts the outer lower eyelid Y to form a small pocket P. The caregiver grasps the bottle 120 at the upper end 150 of the reservoir 151 with a right thumb RG and a right index finger RF, holding the bottle 120 to the side and below the line of vision of the eye E in a near horizontal orientation 22. The caregiver applies digital pressure to the compressible walls 155 of the reservoir 151 and a drop D is instilled into the created pocket P.

One important feature shared by each of these embodiments of bottles 20, 21, 120 is that all the bottles can be held in a substantially horizontal orientation 22 when instilling drops D into an eye E. The bottles 20, 21, 120 all have an internal surface 56, 156 of the walls 55, 155 that maintains a constant slope 58, 158. That slope 58, 158 has a predetermined angle that allows virtually all the liquid 59, 159 in the reservoirs 51, 151, when held in a substantially horizontal orientation 22, to flow toward the dropper tips 34, 134 where it can be released in drop D form by manually expressing the compressible walls 55, 155 of the reservoirs 51, 151 of the bottles 20, 21, 120.

What is claimed is:

1. An eye liquid dispensing bottle configured to allow virtually all the liquid to be discharged therefrom in the form of drops while held in a near horizontal orientation, the bottle comprising in combination:
   (a) a reservoir for holding said liquid;
   (b) said reservoir having an upper end located above a base;
   (c) said upper end having a smaller diameter than said base;
   (d) said reservoir having compressible walls made of a resilient material.

2. The bottle of claim 1 further including a neck beyond said upper end of said reservoir;
   (a) said neck having an opening with a passage to said reservoir;
   (b) said neck permitting a dropper tip to be inserted into said passage;
   (c) said dropper tip having an opening in its center, permitting said liquid in said reservoir to flow externally in said form of drops when digital pressure is applied to said compressible walls of said reservoir.

3. The bottle of claim 1 further including a flange at said upper end of said reservoir;
   (a) said flange encircling said upper end of said reservoir;
   (b) said flange sandwiched between said neck and said upper end of said reservoir of said bottle;
   (c) said flange forming a stop for fingers of a hand to grip against.

4. The bottle of claim 3 wherein said flange being located at a predetermined distance from a distal end of said dropper tip;
   (a) said predetermined distance between said flange and said distal end of said dropper tip providing for alignment and placement of a drop into an eye.

5. The bottle of claim 1 further including external threads on said neck of said reservoir;
   (a) said external threads ending at said flange of said upper end of said reservoir;
   (b) said external threads fitting an internally threaded cap, forming a male-female type locking assembly for said bottle;
   (c) said internally threaded cap tightening against said flange.

* * * * *